United States Patent
Franzetti et al.

(10) Patent No.: US 11,913,041 B2
(45) Date of Patent: *Feb. 27, 2024

(54) METHODS FOR THE MODIFICATION OF PEPTIDES HARBORING AN N-TERMINUS GLYCINE RESIDUE

(71) Applicants: Centre national de la recherche scientifique, Paris (FR); Commissariat à l'énergie atomique et aux énergies alternatives, Paris (FR); UNIVERSITE GRENOBLE ALPES, Saint Martin D'Heres (FR)

(72) Inventors: Bruno Franzetti, Sassenage (FR); Eric Girard, Romans-sur-Isere (FR); Alexandre Appolaire, Grenoble (FR); Hind Basbous, Grenoble (FR)

(73) Assignees: CENTRE NATIONAL DE LA RECHERCHE SCIENTIFIQUE, Paris (FR); COMMISSARIAT À L'ÉNERGIE ATOMIQUE ET AUX ÉNERGIES ALTERNATIVES, Paris (FR); UNIVERSITE GRENOBLE ALPES, Saint Martin D'Heres (FR)

(*) Notice: Subject to any disclaimer, the term of this patent is extended or adjusted under 35 U.S.C. 154(b) by 0 days.

This patent is subject to a terminal disclaimer.

(21) Appl. No.: 17/873,732

(22) Filed: Jul. 26, 2022

(65) Prior Publication Data

US 2023/0049267 A1 Feb. 16, 2023

Related U.S. Application Data

(62) Division of application No. 16/771,752, filed as application No. PCT/EP2018/084632 on Dec. 12, 2018, now abandoned.

(30) Foreign Application Priority Data

Dec. 12, 2017 (EP) .................................... 17306758

(51) Int. Cl.
  *C12N 9/48* (2006.01)
  *A23J 3/34* (2006.01)
  *C12P 21/06* (2006.01)

(52) U.S. Cl.
  CPC .............. *C12N 9/485* (2013.01); *A23J 3/341* (2013.01); *A23J 3/346* (2013.01); *A23J 3/347* (2013.01); *A23J 3/348* (2013.01); *C12P 21/06* (2013.01)

(58) Field of Classification Search
  None
  See application file for complete search history.

(56) References Cited

PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Singh et al. 3 Biotech. Dec. 2016;6(2):174. Epub Aug. 19, 2016 (Year: 2016).*
Accession O58468. Aug. 1, 1998 (Year: 1998).*
Accession A0A832T2K6. Sep. 29, 2021 (Year: 2021).*
Bilal et al., "State-of-the-art protein engineering approaches using biological macromolecules: a review from immobilization to implementation view point." Nov. 2, 2017, 34 pages, Accepted Manuscript, Int J Biol Macromol.
Jamdar, S. N.: "A novel aminopeptidase from Burkholderia cepacia specific for acidic amino acids", 2009, pp. 230-237, vol. 295, FEMS Microbiol Lett.
Marui et al., "Enzymatic properties of the glycine D-alanine [corrected] aminopeptidase of Aspergillus oryzae and its activity profiles in liquid-cultured mycelia and solid-state rice culture (rice koji)", 2012, pp. 655-669, vol. 93, Appln Microbiol Biotechnol.

* cited by examiner

*Primary Examiner* — Christian L Fronda
(74) *Attorney, Agent, or Firm* — B. Aaron Schulman, Esq.; Stites & Harbison, PLLC

(57) ABSTRACT

The invention relates to the uses of a new characterized TET protein showed restricted to N-terminus glycine residues exopeptidase. The invention also relates to a method comprising said use of said new characterized TET protein as a N-terminus glycine residues specific exopeptidase. The invention further relates to a support wherein it is immobilized on said new characterized TET protein as a N-terminus glycine residues specific exopeptidase.

14 Claims, 5 Drawing Sheets
Specification includes a Sequence Listing.

METHODS FOR THE MODIFICATION OF PEPTIDES HARBORING AN N-TERMINUS GLYCINE RESIDUE

CROSS-REFERENCE TO RELATED APPLICATIONS

The present patent application is a divisional application of U.S. Ser. No. 16/771,752, having a filing date of Jun. 11, 2020, which was a National Stage application of International application PCT/EP2018/084632, filed Dec. 12, 2018, which claims priority to European patent application No. 17306758.8 filed Dec. 12, 2017, all of said applications incorporated herein by reference.

SEQUENCE LISTING

The instant application contains a Sequence Listing which has been submitted electronically in XML format under WIPO ST.26 and is hereby incorporated by reference in its entirety. Said XML copy was created on Nov. 3, 2022, is named P12300US01_sequence listing revised.xml, and is 9,019 bytes in size.

FIELD OF THE INVENTION

The invention is related to peptidases and their use.

BACKGROUND OF THE INVENTION

Peptidases are involved in digesting polypeptide chain of peptides and proteins into shorter fragments by splitting the peptide bonds that link amino acid residues. Some detach the terminal amino acids from the protein chain and are called exopeptidases, such as aminopeptidases, carboxypeptidase A; others attack internal peptide bonds of a protein and are called endopeptidases, such as trypsin, chymotrypsin, pepsin, papain, elastase.

Aminopeptidases are enzymes that catalyse the cleavage of amino acids from the amino terminus (N-terminus) of proteins or peptides. They are widely distributed throughout the three-domain system, i.e. archaea, bacteria, and eukaryote domains, and are found in many subcellular organelles, in cytosol, and as membrane components.

Aminopeptidases which are directed to glycine residues, called glycine aminopeptidases (GAPs), are of great interest for the industrial food. Indeed, GAPs are known to better degrade peptides enriched in glycine, which can modify the taste of food preparations from fermentation, like cheeses, the tofu or the sufu. In particular, the release of glycine from the polypeptide chains is of great interest for the Japanese industry because glycine is known to be an enhancer of sweet tastes which are specific to the Japanese gastronomy. The release of the glycine is also important for the flavour of several dry cheeses (feta, parmesan, etc. . . . ).

However, glycine residues are hard to release for aminopeptidases. Nowadays, only three aminopeptidases were found to exhibit clear preference for glycine residues. One of these GAPs is a Zn-dependent metallopeptidase from M61 family secreted by the gram-negative bacteria *Sphingomonas capsulate* (Jamdar, S. N. (2009)). Another one is a eukaryotic S12 family serine peptidase found in the cytosol of *Actinomucor oryzae* (Marui, J., et al. (2012)). The last one is the cytosolic glycyl aminopeptidase of *Actinomucor elegans*, for which the residues implicated in enzymatic mechanism are still ambiguous (Ito K et al. (2003)).

However, these GAPs are not restricted to the glycine residues and show a significant amidolytic activity on other amino acids. Further, these GAPs shows poor yield of production, and come from mesophilic organisms which limits their scope of application.

Therefore, there is a need to provide a new aminopeptidase specific for N-terminus glycine residues, able to operate in industrial conditions.

SUMMARY OF THE INVENTION

The aim of the invention is to obviate these drawbacks.

Thus, the invention relates to the use of a TET protein as a N-terminus glycine residues specific exopeptidase, said TET protein comprising the amino acid sequence as set forth in SEQ ID NO: 1, or any homologous protein derived from said TET protein as set forth in SEQ ID NO: 1 by substitution, addition or deletion of at least one amino acid, provided that the derived protein retains at least 70%, preferably at least 79% of identity with the amino acid sequence as set forth in SEQ ID NO: 1, and said derived protein retaining a N-terminus glycine residues specific exopeptidase activity.

The invention also relates to the use of at least a TET protein harbouring at least a N-terminus glycine residues specific exopeptidase activity, for the modification of all or part of the polypeptide content of a substrate comprising peptides, polypeptides and/or proteins harbouring a N-terminus glycine residue, said at least TET protein comprising the amino acid sequence as set forth in SEQ ID NO: 1, or any homologous protein derived from said at least TET protein as set forth in SEQ ID NO: 1 by substitution, addition or deletion of at least one amino acid, provided that the derived protein retains at least 70%, preferably at least 79% of identity with the amino acid sequence as set forth in SEQ ID NO: 1, and said derived protein retaining a N-terminus glycine residues specific exopeptidase activity.

DETAILED DESCRIPTION

The invention is based on the unexpected characterization by the inventors of a new TET protein as an exopeptidase unambiguously restricted to the cleavage of glycine residues. The inventors surprisingly found that this peptidase is devoid of amidolytic activity on all other amino acid residues except glycine residues. Advantageously, the inventors discovered that this TET protein is a thermophilic protein and can be activated by heat. This is of interest in fermentation industry for example, where the processes are carried out at high temperatures. As a TET protein, this exopeptidase harbours biophysical properties favourable to its immobilization on a support. Consequently, there is advantageously no need for recovering said TET protein in the final preparation, which allows reducing the cost of production of peptides devoid of their glycine N-terminus residues.

Hereafter, the TET protein as set forth in SEQ ID NO: 1 corresponds to the protein PhTET4.

By "exopeptidase", it is meant in the invention a peptidase that catalyses the cleavage of the terminal peptide bond of an amino acid chain, starting either from the amino or carboxyl terminal of the said amino acid chain.

By "peptide", it is meant in the invention an amino acid chain comprising at least 2 amino acids. Peptides can be obtained either from protein degradation or from chemical synthesis. By "polypeptide", it is meant in the invention an amino acid chain larger than a peptide and obtained from degradation of proteins and not from chemical synthesis.

Peptides and polypeptides may harbour biological functions within the context of a protein (signal peptide, death domain, bHLH domain . . . ). By "protein", it is meant in the invention an amino acid chain containing molecule harbouring biological function and which is found naturally in an organism, said biological function being part of a natural process of the cell.

By "at least 70% of identity with the sequence as set forth in SEQ ID NO: 1", it is meant in the invention 70%, 71%, 72%, 73%, 74%, 75%, 76%, 77%, 78%, 79%, 80%, 81%, 82%, 83%, 84% 85% 86% 87% 88% 89% 90% 91%, 92% 93% 94% 95% 96% 97% 98%, 99% and 100% of identity with the sequence as set forth in SEQ ID NO: 1. Regarding the percentage of identity, it is defined by the percentage of amino acid residues of SEQ ID NO: 1 which align with the same amino acid in the sequence of the homologous protein. The sequence alignment is carried out using dedicated algorithms and programs (such as ClustalW, for instance).

In the invention, the term "comprising" is meant to include the terms "consisting essentially of" and "consisting of".

By "modification of all or part of the polypeptide", it is meant in the invention that the modification of a peptide can result in the removal of one or more amino acid from the peptide. If the peptide contains only aromatic amino acids, the peptide can be completely degraded, i.e. can be converted into the free amino acids that constitute the peptide. Moreover, the "modification of all or part of the polypeptide", means also in the invention that, if a composition contains two or more peptides, at least one peptide will be degraded by contacted the TET protein according to the invention. If only some peptides are degraded, the composition of peptide will be considered to be partially modified. If all the peptides are subjected to a degradation, the composition of peptide will be considered to be totally modified. In the invention, regarding a peptide, a polypeptide, a protein or a polypeptide content, the terms "modification" and "degradation" can be used uniformly.

Advantageously, said TET protein or said derived protein originates from an extremophilic microorganism belonging to the Thermococcales order and is isolated from this extremophilic microorganism. By "extremophilic", it is meant in the invention an organism that thrives in physically or geochemically extreme conditions that are detrimental to most life on Earth. In contrast, organisms that live in more moderate environments may be termed mesophiles or neutrophiles. Among the hyperthermophilic archaea, representatives of order Thermococcales form the most numerous group to date. Members of this group are the most frequently isolated hyperthermophilic archaea. They are heterotrophic and as such regarded as the major constituents of organic matter within marine hot water ecosystems. They belong to the branch of Euryarchaeota that contains the methanogens, the genus *Thermoplasma*, and the extremely halophilic archaea. The Thermococcales order is actually represented by three genera: *Pyrococcus, Thermococcus* and the newly described Paleococcus.

Advantageously, said extremophilic microorganism is *Pyrococcus horikoshii*.

Advantageously, peptides, polypeptides and/or proteins of said substrate are obtained from food industry or health industry or chemical industry. Advantageously, proteins from fermented products or soya products or sea food products or cheese products.

The generation of protein-rich industrial wastes is very high (only from sunflower, about one million tons in Spain). These wastes are not used at all, or are underused in the form of low added-value products. This type of by-products constitutes a reservoir of proteins with a great economic potential.

The TET protein according to the invention, in view of its activity, can be used in various domains for instance, but without limitation:

For the valorization of agriculture wastes: proteins and peptides originating from agriculture can be recycled for animal feed, or for producing feed additives. In order to be used, the vegetal proteins have to be degraded to avoid any antinutritional side effects.

For the valorization of chemical wastes

For the valorization of food industry waste: suitable proteins to be treated with the TET aminopeptidase according to the invention may be for instance proteins obtained from dairy products, fruit juices, beers, flours or cured products. Moreover, the products from wine industry, from cheese industry, and see food industry are particularly advantageous and can be valorized by using the TET protein according to the invention.

Products from biomass: some alternative to common protein sources are now emerging in view of the need to provide more and more feed for the Earth population. For instance, algae and microorganisms, along with insects, are very rich in protein that can be used for providing new sources of amino acids or proteins that can be eaten by animal and humans. Therefore, proteins or peptides from algae or microorganisms can be relevant sources for treatment by using the TET protein according to the invention.

Another kind of wastes are the wastes produced from health industry. For instance, solid, regulated medical waste can includes materials generated in the diagnosis, treatment, research, or immunization of human beings or animals. Examples of regulated medical waste includes: cultures and stocks, pathological wastes, human blood and blood products, sharps, certain animal waste and isolation wastes. The TET protein according to the invention may help to valorize such kinds of wastes.

The invention also relates to a method for degrading, from the N-terminus part, a polypeptide harbouring a glycine residue at its N-terminal part, said method comprising a step of contacting said polypeptide harbouring a glycine residue at its N-terminal part with at least a TET protein harbouring at least a N-terminus glycine residues specific exopeptidase activity, said TET protein comprising the amino acid sequence as set forth in SEQ ID NO: 1, or at least one homologous protein derived from said TET protein as set forth in SEQ ID NO: 1 by substitution, addition or deletion of at least one amino acid, provided that the derived protein retains at least 70%, preferably at least 79% of identity with the amino acid sequence as set forth in SEQ ID NO: 1, and said derived protein retaining a N-terminus glycine residues specific exopeptidase activity, and optionally a step of recovering the resulting N-terminal glycine free peptides.

The invention also relates to a method for modifying all or part of the polypeptide content of a substrate comprising peptides, polypeptides and/or proteins, wherein at least one of the peptides, polypeptides and/or proteins of said substrate harbours a N-terminus glycine residue, said method comprising a step of contacting said substrate with at least a TET protein harbouring at least a N-terminus glycine residues specific exopeptidase activity, said TET protein comprising the amino acid sequence as set forth in SEQ ID NO: 1, or at least one homologous protein derived from said TET protein as set forth in SEQ ID NO: 1 by substitution, addition or deletion of at least one amino acid, provided that the derived protein retains at least 70%, preferably at least 79% of identity with the amino acid sequence as set forth in SEQ ID NO: 1, and said derived protein retaining a N-terminus glycine residues specific exopeptidase activity, and optionally a step of recovering the modified polypeptide content of said substrate.

Advantageously, in the method for modifying all or part of the polypeptide content of a substrate comprising peptides, polypeptides and/or proteins harbouring a N-terminus glycine residue, said step of contacting comprises the activation of the said TET protein or derived protein using as enzyme cofactor at least one of the metal ions of the group consisting of $Ni^{2+}$, $Co^{2+}$ and $Mn^{2+}$, preferably using $Ni^{2+}$ as enzyme cofactor. This aspect of the invention is interesting because $Ni^{2+}$ is a rare cofactor of aminopeptidase. Indeed, most of the aminopeptidases are activated by $Zn^{2+}$ cofactor. Consequently, PhTET4 can be selectively activated in a pool of aminopeptidases.

In particular, said step of contacting is carried out from pH 9 to pH 10, provided that the aminopeptidase activity of said at least TET protein or said derived protein being maintained to a aminopeptidase activity of at least 80% of their maximum activity. Advantageously, said step of contacting is carried out at least at pH 9. By "at least at pH 9", it is meant in the invention pH 9, pH 9.1, pH 9.2, pH 9.3, pH 9.4, pH 9.5. Advantageously, said step of contacting is carried out at most at pH 10. By "at most at pH 10", it is meant in the invention pH 10, pH 9.9, pH 9.8, pH 9.7, pH 9.6. Advantageously said step of contacting is carried out at pH 9.5.

Advantageously, said step of contacting is carried out from 80° C. to 100° C., provided that the aminopeptidase activity of said at least TET protein or said derived protein being maintained to an aminopeptidase activity of at least 80% of their maximum activity. Advantageously, said step of contacting is carried out at least at 80° C. By "at least at 80° C.", it is meant in the invention, 80° C., 80.1° C., 80.2° C., 80.3° C., 80.4° C., 80.5° C., 80.6° C., 80.7° C., 80.8° C., 80.9° C., 81° C., 81.1° C., 81.2° C., 81.3° C., 81.4° C., 81.5° C., 81.6° C., 81.7° C., 81.8° C., 81.9° C., 82° C., 82.1° C., 82.2° C., 82.3° C., 82.4° C., 82.5° C., 82.6° C., 82.7° C., 82.8° C., 82.9° C., 83° C., 83.1° C., 83.2° C., 83.3° C., 83.4° C., 83.5° C., 83.6° C., 83.7° C., 83.8° C., 83.9° C., 84° C., 84.1° C., 84.2° C., 84.3° C., 84.4° C., 84.5° C., 84.6° C., 84.7° C., 84.8° C., 84.9° C., 85° C. Advantageously, said step of contacting is carried out at most at 100° C. By "at most at 100° C.", it is meant in the invention 100° C., 99.9° C., 99.8° C., 99.7° C., 99.6° C., 99.5° C., 99.4° C., 99.3° C., 99.2° C., 99.1° C., 99° C., 98.9° C., 98.8° C., 98.7° C., 98.6° C., 98.5° C., 98.4° C., 98.3° C., 98.2° C., 98.1° C., 98° C., 97.9° C., 97.8° C., 97.7° C., 97.6° C., 97.5° C., 97.4° C., 97.3° C., 97.2° C., 97.1° C., 97° C., 96.9° C., 96.8° C., 96.7° C., 96.6° C., 96.5° C., 96.4° C., 96.3° C., 96.2° C., 96.1° C., 96° C., 95.9° C., 95.8° C., 95.7° C., 95.6° C., 95.5° C., 95.4° C., 95.3° C., 95.2° C., 95.1° C., 95° C., 94.9° C., 94.8° C., 94.7° C., 94.6° C., 94.5° C., 94.4° C., 94.3° C., 94.2° C., 94.1° C., 94° C., 93.9° C., 93.8° C., 93.7° C., 93.6° C., 93.5° C., 93.4° C., 93.3° C., 93.2° C., 93.1° C., 93° C., 92.9° C., 92.8° C., 92.7° C., 92.6° C., 92.5° C., 92.4° C., 92.3° C., 92.2° C., 92.1° C., 92° C., 91.9° C., 91.8° C., 91.7° C., 91.6° C., 91.5° C., 91.4° C., 91.3° C., 91.2° C., 91.1° C., 91° C., 90.9° C., 90.8° C., 90.7° C., 90.6° C., 90.5° C., 90.4° C., 90.3° C., 90.2° C., 90.1° C., 90° C., 89.9° C., 89.8° C., 89.7° C., 89.6° C., 89.5° C., 89.4° C., 89.3° C., 89.2° C., 89.1° C., 89° C., 88.9° C., 88.8° C., 88.7° C., 88.6° C., 88.5° C., 88.4° C., 88.3° C., 88.2° C., 88.1° C., 88° C., 87.9° C., 87.8° C., 87.7° C., 87.6° C., 87.5° C., 87.4° C., 87.3° C., 87.2° C., 87.1° C., 87° C., 86.9° C., 86.8° C., 86.7° C., 86.6° C., 86.5° C., 86.4° C., 86.3° C., 86.2° C., 86.1° C., 86° C., 85.9° C., 85.8° C., 85.7° C., 85.6° C., 85.5° C., 85.4° C., 85.3° C., 85.2° C., 85.1° C. Advantageously said step of contacting is carried out at 85° C. Carried out amidolytic activity at high temperature is interesting in industry, because one use of the TET protein is about fermentation which is also carried out at high temperature. Moreover, the TET protein is heat activatable and can be therefore specifically activated during the fermentation step of an industrial process.

Compared to other TET family member peptidases, the TET protein according to the invention is active at a pressure varying from 0.1 MPa to 350 MPa.

Advantageously, said at least TET protein or said derived protein is immobilized on a solid support. As abovementioned, the biophysical properties of a TET protein allow its use on a support. Consequently, in an industrial process for a final preparation, the TET protein can be put into contact with the substrate without mixing them together so that there is no need to recover said TET protein in the final preparation. Advantageously, said at least TET protein or said derived protein is immobilized on a filter cartridge or on silica beads or on magnetic beads or on organic polymeric materials, or on inorganic polymeric materials or on membrane devices or in microcapsules. Membrane devices include hollow fibers.

In view of the robustness of the TET protein, and the stability of the structure, it is possible to immobilized the TET protein on a support. Such a support is advantageous and allows to carry out a peptide, polypeptide or peptide degradation and recover the resulting degraded peptide, polypeptides and protein, easily without additional step of separation of the enzyme and the resulting product. Current enzyme immobilization methods are described in the review of Bilal et al. (Bilal M, Iqbal H M, Guo S, Hu H, Wang W, Zhang X (2017) State-of-the-art protein engineering approaches using biological macromolecules: A review from immobilization to implementation view point. Int J Biol Macromol. November 2.).

The invention is further related to the use of a solid support for the modification of all or part of the polypeptide content of a substrate comprising peptides, polypeptides and/or proteins, wherein at least one of the peptides, polypeptides and/or proteins of said substrate harbours a N-terminus glycine residue, and wherein is immobilized on said solid support at least a TET protein harbouring at least a N-terminus glycine residues specific exopeptidase activity, said TET protein comprising the amino acid sequence as set forth in SEQ ID NO: 1, or at least one homologous protein derived from said TET protein as set forth in SEQ ID NO: 1 by substitution, addition or deletion of at least one amino acid, provided that the derived protein retains at least 70%, preferably at least 79% of identity with the amino acid sequence as set forth in SEQ ID NO: 1, and said derived protein retaining a N-terminus glycine residues specific exopeptidase activity.

Advantageously, said solid support is a filter cartridge or silica beads or magnetic beads or on organic polymeric materials, or on inorganic polymeric materials or on membrane devices or in microcapsules. Membrane devices include hollow fibers.

Advantageously, peptides, polypeptides and/or proteins of said substrate are obtained from food, chemical and health industries, or from biomass, as mentioned above. Advantageously, proteins from fermented products or soya products or sea food products or cheese products.

Alternatively, said at least TET protein or said derived protein is immobilized as cross-linked enzyme aggregates (CLEAs).

CLEAs are developed by precipitation of the enzyme from a solution by adding salt, such as ammonium sulphate, or water-miscible organic solvent, followed by cross-linking with a bifunctional reagent (Bilal M, Iqbal H M, Guo S, Hu H, Wang W, Zhang X (2017) State-of-the-art protein engineering approaches using biological macromolecules: A review from immobilization to implementation view point. Int J Biol Macromol. November 2.).

The invention will be better understood from the following example and the 8 following figures.

BRIEF DESCRIPTION OF THE DRAWING FIGURES

FIG. 1 is a sequence alignment of PhTET1, 2, 3 and 4. Conserved residues are in a grey box and similar residues are boxed. The numbering and the secondary structure elements are those of PhTET1 (PDB ID: 2WYR). Light grey stars and heavy grey starts highlight the metal-binding and active residues, respectively.

In FIG. 2A, X-axis represents the volume (ml) of exclusion and Y-axis represents the absorbance (mAU) at 280 nm.

Figure 6:
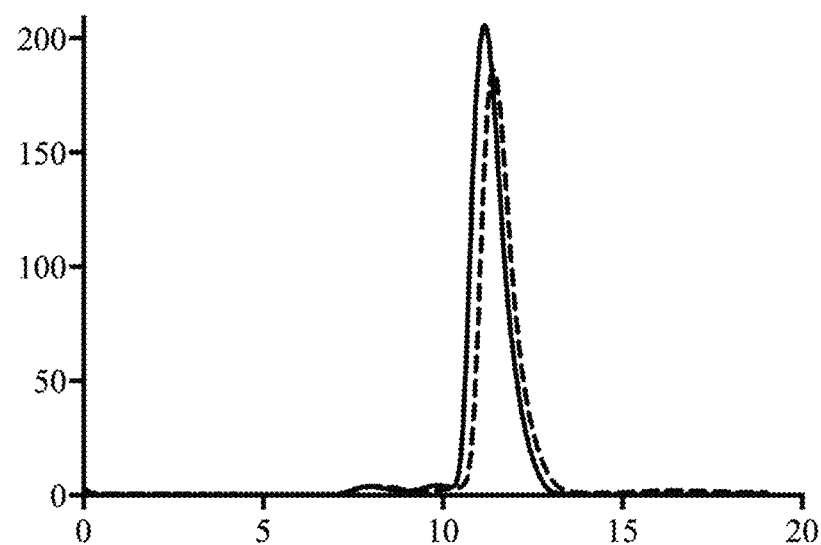

FIG. 6 represents the size exclusion chromatography of PhTET4 in absence or presence of EDTA. The continuous line represents the size exclusion chromatography of PhTET4 in absence of EDTA. The discontinuous line represents the size exclusion chromatography of PhTET4 in presence of EDTA. X-axis represent the volume (ml) of exclusion. Y-axis represents the absorbance (mAU) at 280 nm.

Figure 7:
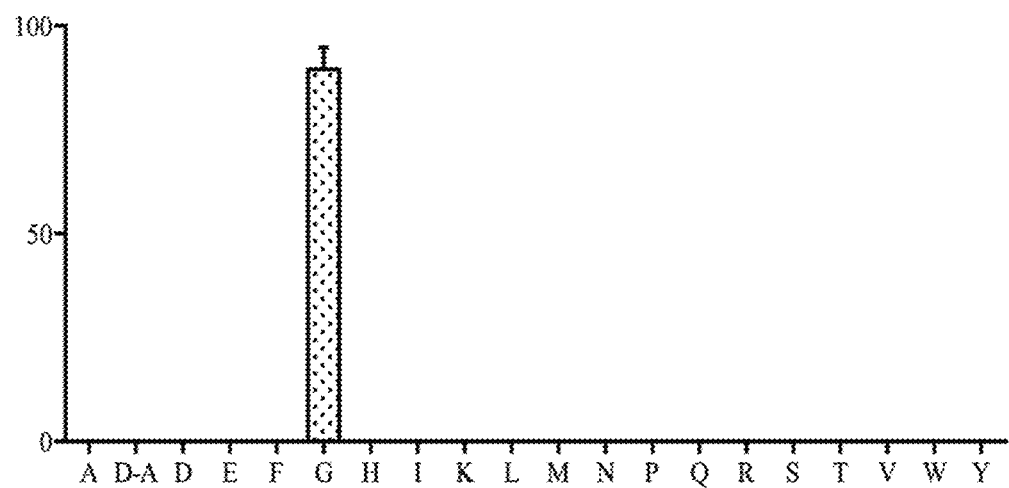

FIG. 7 is a graph representing the relative amidolytic activity of PhTET4 on L-Alanine (A), D-Alanine (D-A), L-Aspartate (D), L-Glutamate (E), L-Phenylalanine (F), L-Glycine (G), L-Histidine (H), L-Isoleucine (I), L-Lysine (K), L-Leucine (L), L-Methionine (M), L-Asparagine (N), L-Proline (P), L-Glutamine (Q), L-Arginine (R), L-Serine (S), L-Threonine (T), L-Valine (V), L-Tryptophan (W), and L-Tyrosine (Y). Y-axis represents the relative activity (%) of PhTET4.

Figure 8A:
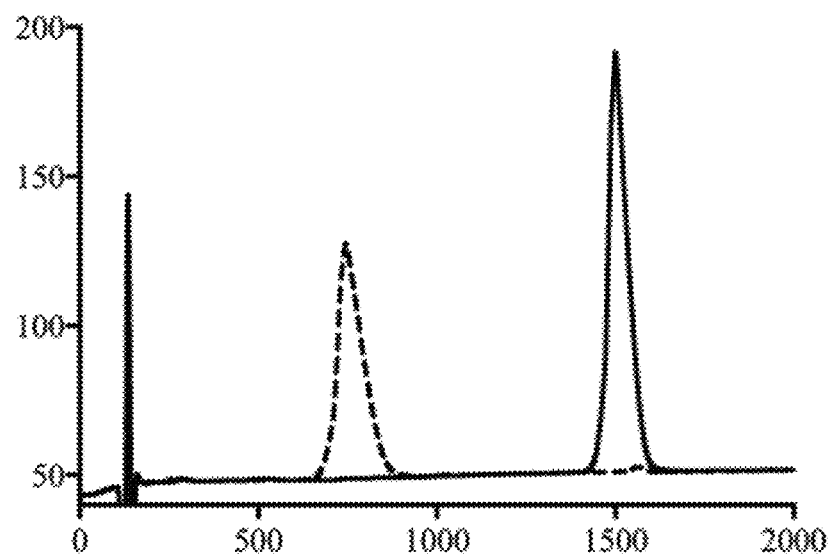
Figure 8B:
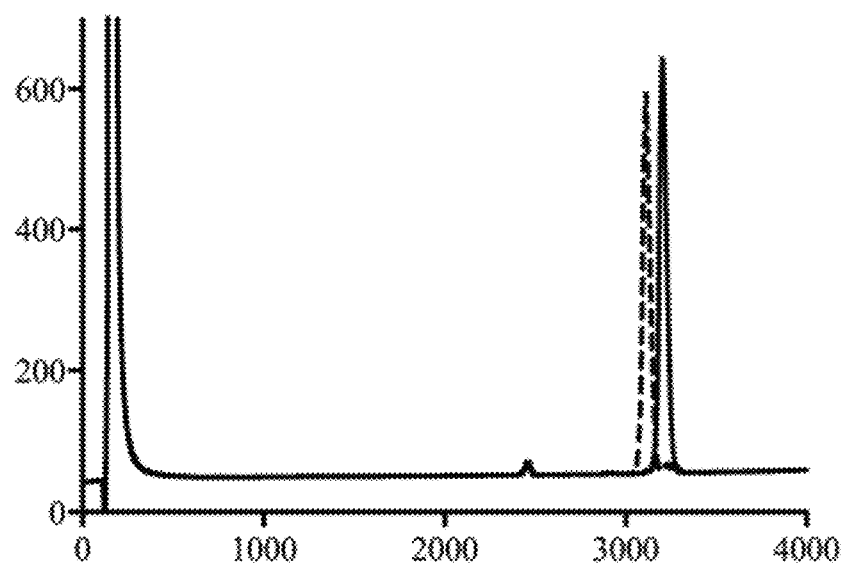

FIGS. 8A and 8B are provided wherein FIG. 8A represents the size exclusion chromatography of GLM. FIG. 8B represents the size exclusion chromatography of GMD-SLAFSGGL (SEQ ID NO: 6) peptides, respectively, after incubation with PhTET4. In both figures, the continuous line represents the size exclusion chromatography of the intact peptide, and the discontinuous line represents size exclusion chromatography of the said peptide cleaved by PhTET4. X-axis represents the elution time (sec). Y-axis represents the Absorbance (mAU) at 214 nm.

EXAMPLE

Methods
PhTET4 Expression and Purification

The gene encoding for PH0737 (SEQ ID NO: 5) was cloned in pET-41c vector GeneCust Europe, Luxembourg. Recombinant protein was overexpressed in *Escherichia coli* BL21 (DE3)-RIL strain during 4 hours at 37° C. by induction with 0.1 mM IPTG in 1 L of lysogeny broth medium. The cell pellet was conserved at −80° C. until using. The cells were re-suspended in 25 mL Tris-HCl 50 mM pH 8, NaCl 90 mM and Triton X-100 0.1%, supplemented with 6.25 mg lysozyme (Euromedex), 1.25 mg DNase I grade II (Roche), 5 mg RNase (Roche), 25 mg Pefabloc SC (Roche) and 0.25 mL MgSO4 at 2 M. Cells were disrupted by sonication at 30 watts with 5 cycles on/off of 30 sec each at 4° C., and then heated for 20 min at 75° C. to eliminate most mesophilic proteins of host strain. The lysate was clarified by centrifugation at 12,000 rpm, 4° C. for 1 hour with JA20 rotor (Beckman), and the supernatant was loaded on ResourceQ column (GE healthcare) equilibrated with 20 mM Tris-HCl pH 7.5, 100 mM NaCl. The 30 mL of the flow-through were retained and diluted with 20 mL Tris-HCl pH 7.5 to a final concentration of 105 mM NaCl. The new supernatant volume was loaded a second time on ResourceQ column. After washing the column with 20 mM Tris-HCl pH 7.5, 100 mM NaCl, bound proteins were eluted with linear salt gradient (154-290 mM NaCl). The protein-contained fractions were pooled together and loaded on Superdex200 10/300 GL size exclusion column (GE healthcare) equilibrated with 20 mM Tris-HCl pH 7.5, 150 mM NaCl. PhTET4 protein was eluted at 11 mL of column exclusion volume. The peak fractions were combined and concentrated with Amicon Ultra 30 kDa cut-off and stored at 4° C. The purity of prepared protein was checked by SDS-PAGE. 3 mg of PhTET4 were produced from 1 L of culture.

PhTET4 Negative Stain Electron Microscopy

After the size exclusion chromatography step, 4 μl of PhTET4 at 0.05 mg/ml were deposited onto carbon-coated 400-mesh copper grids. The samples were stained using uranyl acetate 2% and air-dried. Images were taken under low-dose conditions in a T12FEI electron microscope working at 120 kV and with a nominal magnification of 40,000 using an Orius SC1000 CCD camera.

PhTET4 Substrate Specificity

The hydrolytic activity of PhTET4 was determined by using chromogenic and fluorogenic compounds: aminoacyl-pNAs (p-Nitroaniline) and aminoacyl-AMCs (7-Amino-4-methylcoumarin), respectively. Reactions were initiated by addition of 4 μg/ml (final concentration) of PhTET4 to 400 μl of pre-warmed mixture containing 5 mM chromogenic or fluorogenic substrate in 50 mM PIPES, 150 mM KCl, pH 7.5 at 80° C. Since all tetrahedral aminopeptidases of *P. horiko-*

*shii* are activated by cobalt, the inventors started by using 0.1 mM CoCl2 as metal activator for PhTET4 enzymatic activity. Then, the experimentation was later repeated using the determined optimal conditions (0.1 mM NiCl2, pH 9.5 and at 85° C.). In order to avoid water evaporation, the total volume was covered by a layer of mineral oil. Catalytic activity was followed during 10 min by measuring the absorbance of released pNA at 405 nm or the AMC fluorescence using excitation and emission wavelengths of 355 and 460 nm, respectively.

PhTET4 Metallic Cofactor

In presence of cobalt low activity was identified against Gly-pNA. So, in order to enhance the enzymatic activity of PhTET4, several divalent metals were tested at 0.1 mM final concentration in a reaction volume containing 4 µg/ml PhTET4, 50 mM CHES, 150 mM KCl and 5 mM Gly-pNA, pH 9.5. The reaction was followed at 80° C. by measuring the absorbance of released pNA at 405 nm during 10 min.

PhTET4 Optimal pH

The effect of pH on PhTET4 enzymatic activity was studied by using different buffers: PIPES, pH 6-7.5; CHES, pH 8.2-10 and CAPS, pH 10.5-11. All buffers were used at 50 mM final concentration in presence of 4 µg/ml PhTET4, 150 mM KCl, 0.1 mM NiCl2 and 5 mM Gly-pNA at 80° C. The incubation was done for 10 min by measuring the absorbance of released pNA at 405 nm.

PhTET4 Optimal Temperature

The temperature impact on the enzymatic activity of PhTET4 was measured in a range from 20 to 95° C. In all cases, 4 µg/ml of PhTET4 were incubated with 50 mM CHES, 150 mM KCl, 0.1 mM NiCl2 and 5 mM Gly-pNA, pH 9.5 during 10 min. The reaction was assessed as described previously.

Peptide Substrates

More enzymatic studies were performed to decipher PhTET4 cleavage activity by using peptide substrates (GI; GL; GLM; GMDSLAFSGGL (SEQ ID NO: 6); LGG). 6 µg/ml (final concentration) of PhTET4 were added to a pre-warmed mixture of 3 mM peptide, 50 mM CHES, 150 mM KCl, 0.1 mM NiCl2, pH 9.5. To avoid water evaporation, 20 µl of mineral oil were added on the top of the total volume. The reaction incubation was done at 85° C. during 6 min. Aliquot of 80 µl was then removed and added to 220 µl of 2% acetonitrile (ACN), 0.1% trifluoroacetic acid (TFA). Proteins were removed by centrifugation at 13,000 rpm during 15 min. 100 µl of the supernatant were retrieved and injected on Nova-Pak C18 column, (4 µm, 3.9×300 mm, (Waters)) in a HPLC purifier system (PerkinElmer), equilibrated with 2% ACN, 0.1% TFA. The elution of peptide products was achieved with a linear ACN gradient (2-33.2%) and followed by measuring the absorbance at 214 nm. Chromatographic runs were carried out at room temperature. The separated fragments were collected and submitted to N-terminal sequence analysis.

PhTET4 Inhibition

PhTET4 was incubated in presence of 5 mM EDTA, 50 mM CHES, 150 mM KCl, pH 9.5 at 85° C. during 15 min. Then, the oligomeric state of inhibited protein was evaluated by using exclusion chromatography column (Superdex200) equilibrated with the same incubation buffer: 50 mM CHES, 150 mM KCl, pH 9.5.

Results

In all cell types, metallo-aminopeptidases play crucial roles in energy metabolism, protein maturation and degradation and in the regulation of biologically active peptides by removing the N-terminal amino acid from proteins and oligopeptides. Overall, metalloenzymes all have one feature in common, namely that the metal ion is bound to the protein with one labile coordination site. As with all enzymes, the shape of the active site is crucial. The metal ion is usually located in this active site or in the catalytic pocket. In most of case, metallo-aminopeptidases operate beyond the action of an endoprotease and their activity is limited to small peptides.

Several aminopeptidases assemble as large dodecameric particles, first discovered in archaea and named TET due to their peculiar tetrahedral shapes. The 13 nm hollow dodecahedrons enclose 12 active sites distributed in 4 funnel-shaped chambers located in the apices of the particles and four large access holes, formed by the junction of six subunits, situated in the facets. This organization strongly distinguishes TET from the other cytosolic compartmentalized peptidases that mostly adopt a barrel-shaped architecture.

Biochemical and structural studies of TET peptidases have accumulated over the past 10 years. They revealed that TET dodecamers represent a common scaffold for an efficient polypeptide capture and processing system. In all TET, the aminopeptidase activity is based on co-catalytic dinuclear metal active site belonging to M18 or M42 peptidase families according to MEROPS peptidase database. Bounding peptides are cleaved following common mechanism involving water molecule and glutamate residue. The nature of the metal occupying the bimetallic active site has been shown to modulate TET enzymatic activity and $Co^{2+}$ ions appear to be the best activators for almost all archaeal and bacterial M42 TET.

TET machines are widespread and were found in the three life domains. Interestingly, in prokaryotes, 1 to 4 different types of TET complexes can co-exist in the cytosol depending upon the cell type. These enzymes can be categorized according to their preference for the chemical structure of the N-terminal amino acid residues present in the polypeptide chains. Three main categories have been identified so far: glutamyl/aspartyl aminopeptidases, lysine aminopeptidases and leucine aminopeptidases, these later exhibiting the broader specificities. In eukarya, M18 TET complexes displayed aspartyl aminopeptidase activity. In bacteria, M42 TET peptidases, from *Clostridium thermocellum* and *Thermotoga maritima*, were assigned as leucyl aminopeptidases. Two M42 enzymes from the pathogens *Streptococcus pneumoniae* and *Mycoplasma hyopneumoniae* displayed glutamyl-aminopeptidase activities. In archaea, the common TET structural scaffold can harbour disparate functions. So far, the unique TET complex described in the halophilic archaeon *Haloarcula marismortui* displayed the broader specificities with a preference for neutral and basic residues.

1. Characterisation of a New TET Protein, PhTET4

*Pyrococcus horikoshii* is a deep-sea hyperthermophilic archaeon belonging to the Thermococcales order that was isolated at 1395 m depth from a hydrothermal vent. *P. horikoshii*, and other related hyperthermophilic Thermococcales are distinguished by the fact that they possess three different TET complexes: PhTET1 (SEQ ID NO: 2), a glutamyl/aspartyl aminopeptidase, PhTET2 (SEQ ID NO: 3), a leucyl aminopeptidase with a broad activity against neutral amino-acids and PhTET3 (SEQ ID NO: 4), a lysyl aminopeptidase with a clear preference for positively charged residues. The analysis of their activities on synthetic peptides of different sizes and compositions using reverse phase HPLC indicated that the TET peptidases degrade oligopeptides in a sequential manner and displayed strict aminopeptidase behaviour.

Figure 1:
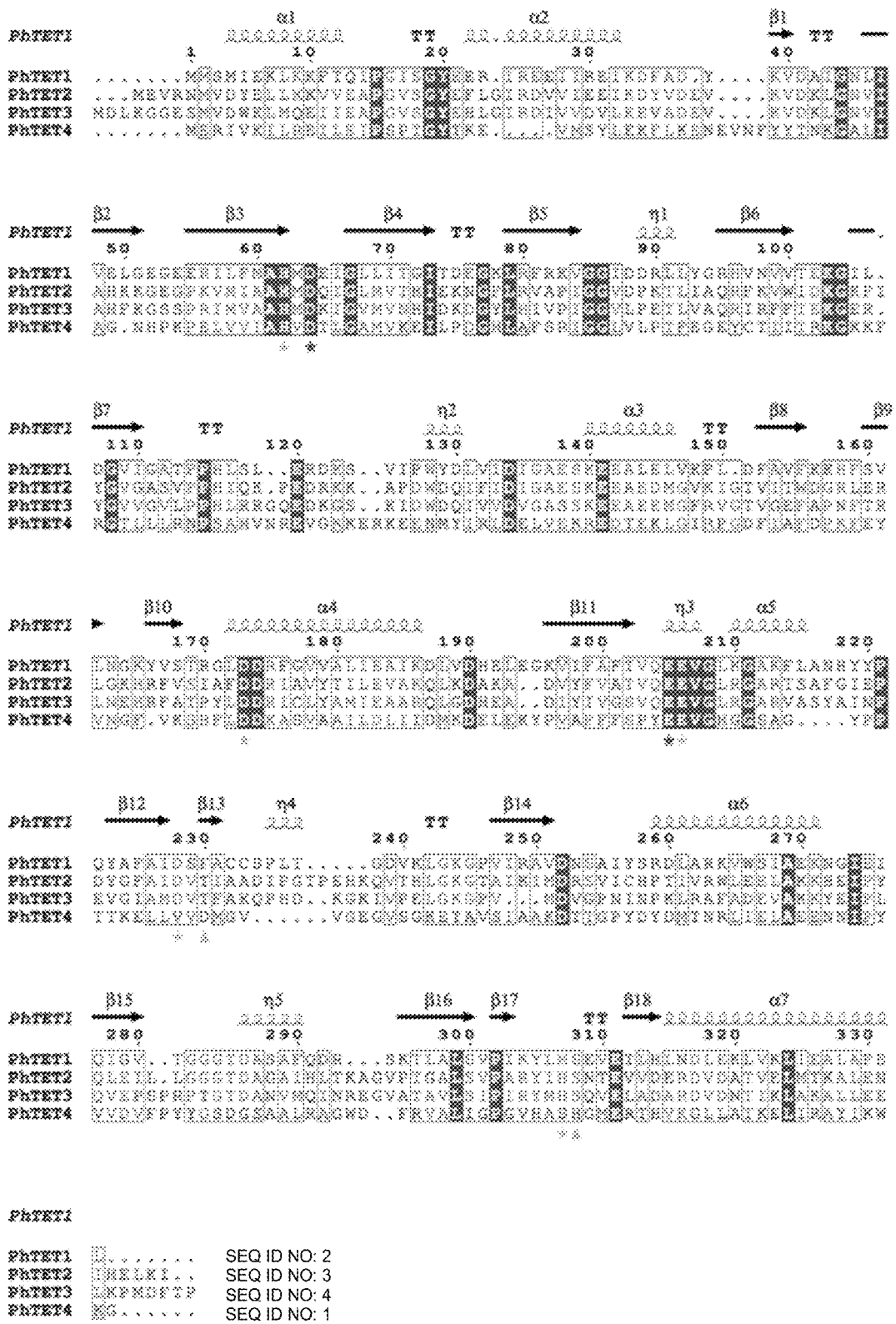

An analysis of the genomes of *P. horikoshii* revealed the existence of a conserved gene PH0737 encoding for an unassigned peptidase of MH clan in MEROPS peptidase database. The protein encoded by PH0737 gene shares 20.6%, 22.5% and 22% of sequence identity with the three characterized aminopeptidases PhTET1, PhTET2 and PhTET3 respectively (FIG. 1). The residues involved in the coordination of metal ions in M42 peptidase family are well conserved between PhTET1, 2, 3 and the said unassigned peptidase. Moreover, the unassigned peptidase comprises two regions (the catalytic domain and the little β sheet domain localized on the top of the former) that conferring the ability of M42 peptidases to form large multimers. Most likely, a shift was occurred for the two latest putative ligands of the unassigned peptidase, Asp231 and His311, which are highlighted by light grey triangle in comparison with the conserved position of PhTET1, 2 and 3 ligands. Hence, said unassigned peptidase was named PhTET4. PhTET4 refers to SEQ ID NO: 1.

2. Determination of the Three-Dimensional Structure of PhTET4

Figures 2A, 2B:
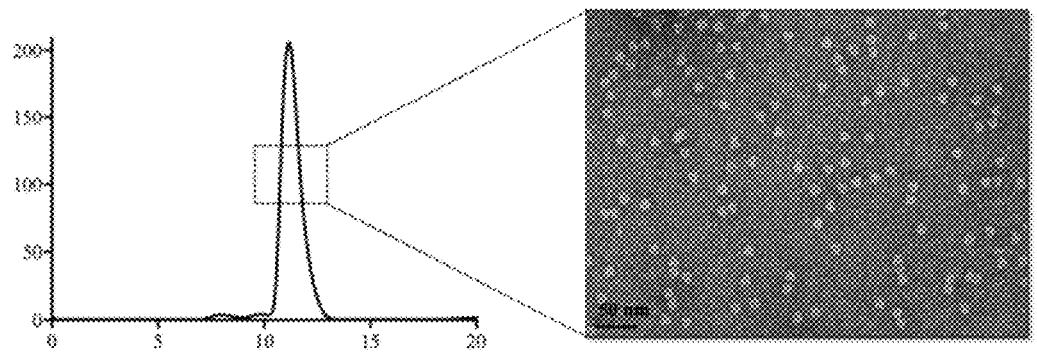
FIGS. 2A and 2B are respectively an elution profile of PhTET4 on size-exclusion chromatography column (superdex200 10/300 GL), and a micrograph of the said eluted PhTET4 observed by negative strain electron microscopy.

The three-dimensional structure of PhTET4 was assessed by producing the recombinant PhTET4 in *E. coli*. The cellular extract was clarified by heat shock precipitation and the recombinant protein was purified by ion-exchange and size-exclusion chromatographies. At the final step, PhTET4 was eluted at the same exclusion volume (11 mL) than PhTET1 to 3, suggesting that it forms large molecular weight assembly similar to the ~500 kDa TET dodecameric complexes (FIG. 2A). Negative stain electron microscopy micrographs realized on PhTET4 peak fractions, showed that the protein self-assembled in a hollow tetrahedral-shaped complex of homogenous size (FIG. 2B). The dimensions and the shape of PhTET4 are analogous to the three *P. horikoshii* tetrahedral TET edifices: PhTET1, PhTET2 and PhTET3.

3. Characterisation of PhTET4 Amidolytic Activity

To determine PhTET4 functional identity the inventors tested its amidolytic activity toward the 20 amino acids by using a broad array of chromogenic p-nitroaniline (pNA) or fluorogenic 7-amino-4-methylcoumarin (AMC) conjugated aminoacyl compounds. Because of the homologies between phTET4 with PhTET1, 2 and 3, the inventors first test the amidolytic activity of PhTET4 using the known operative conditions of PhTET1, 2 and 3. $Co^{2+}$ being the main activating metal of the 3 TET enzymes from *P. horikoshii*, the inventors first assayed PhTET4 activity in the presence of 0.1 mM $CoCl_2$ as enzyme cofactor, at 80° C. and in identical buffer conditions (5 mM substrate, 50 mM PIPES, 150 mM KCl, pH 7.5). Surprisingly, the results showed that no hydrolysis was observed against all tested substrates with the notable exception of Gly-pNA toward which PhTET4 exhibited a weak catalytic activity.

4. Characterisation of PhTET4 Operatives Conditions a) Metal Cofactors

Figure 3:
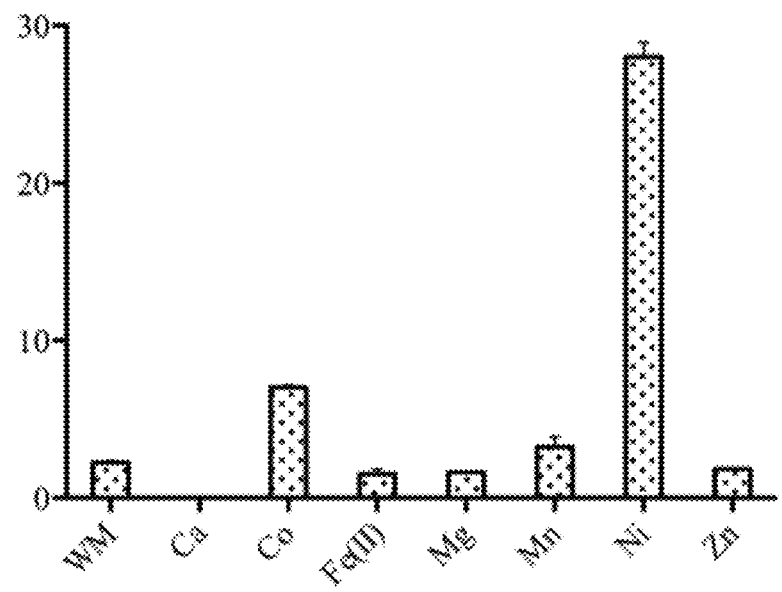
FIG. 3 is a graph representing the variation of PhTET4 specific activity in the absence (WM) of metal, or in the presence of ions Calcium (Ca), Cobalt (Co), Fer (FeII), Magnesium (Mg), Nickel (Ni), and Zinc (Zn). Y-axis represent the specific activity of PhTET4 (pmol (pNA) mg-1 (PhTET4) min-1). pNA stands for p-Nitroaniline.

Since metal cofactors have been shown to be essential to control the activity and the oligomeric state of the various TET edifices characterized so far, the inventors tested the influence of various metal ions on PhTET4 glycyl aminopeptidase activity. The results are shown on FIG. 3. Surprisingly, the inventors revealed that $Ni^{2+}$ shows the most important stimulating effect on PhTET4 cleavage activity, with 12 times greater activity compared with control assay where no metallic ion (WM) was added to the reaction volume. $Co^{2+}$ and $Mn^{2+}$ also stimulated PhTET4 activity but less efficiently than $Ni^{2+}$ (3 and 1.4 fold activation, respectively). Interestingly, $Zn^{2+}$, $Ca^{2+}$, $Fe^{2+}$ and $Mg^{2+}$ were found to inhibit PhTET4 hydrolytic activity, and total inhibition was observed in presence of $Ca^{2+}$ ions. This is the first time that $Ni^{2+}$ ions have been described as an essential activating cofactor of an aminopeptidase from the M42 family. This is an advantage and allow user to selectively activate PhTET4 in a pull of peptidases.

b) pH Conditions

Figure 4:
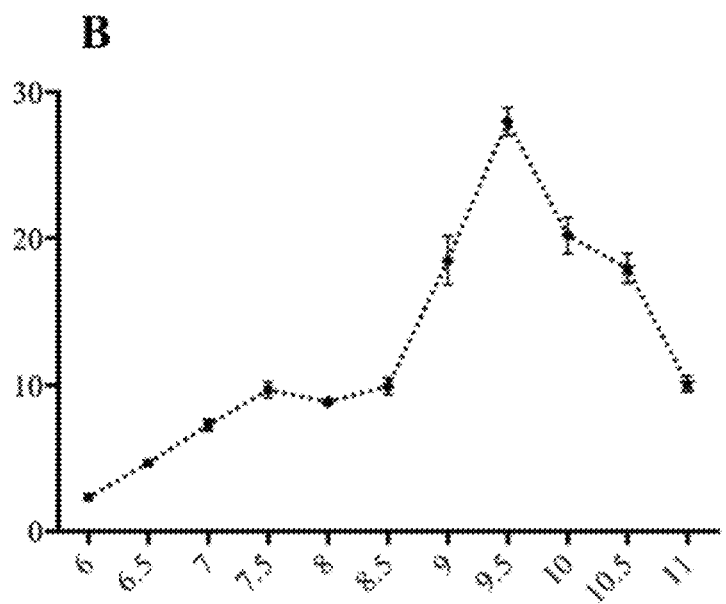
FIG. 4 is a graph representing the evolution of PhTET4 specific activity from pH 6 to pH 11. Y-axis represent the specific activity of PhTET4 (pmol (pNA) mg-1 (PhTET4) min-1). pNA stands for p-Nitroaniline.

In order to determine the influence of pH on PhTET4 enzymatic behaviour, the amidolytic activity was measured between pH 6 and pH 11, against Gly-pNA at 80° C. The results are shown on FIG. 4. The optimal activity was found at pH 9.5 and a significant percentage of activity (beyond 80% of the maximal activity) was observed from pH 9 to pH 10. Consequently, a significant percentage of activity is maintained at elevated pH. These experiments revealed that, compared to the other 3 PhTETs enzymes, PhTET4 can be defined as an alkaline peptidase.

c) Temperature Conditions

Figure 5:
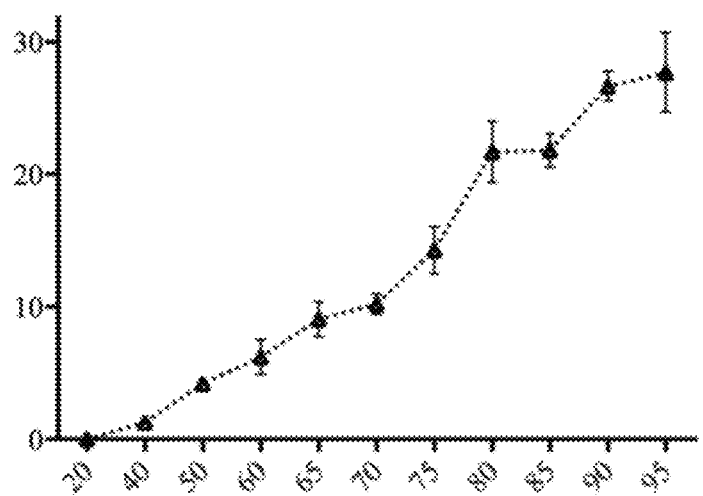
FIG. 5 is a graph representing the evolution of PhTET4 specific activity from 20° C. to 95° C. Y-axis represent the specific activity of PhTET4 (pmol (pNA) mg-1 (PhTET4) min-1). pNA stands for p-Nitroaniline.

To assess the hyperthermophilic properties of the enzyme, the temperature dependence of PhTET4 activity was studied at different temperatures varying from 20 to 95° C. The results are shown on FIG. 5. PhTET4 enzymatic activity increases in parallel with the augmentation of heating temperature, with a maximal activity observed at 95° C. in the measurable temperature range. A significant percentage of activity (beyond 80% of the maximal activity) was observed from 80° C. to 95° C. Thus PhTET4 displays a high hyperthermophilic behaviour comparable to the ones reported for the 3 other PhTETs aminopeptidases present in *Pyrococcus horikoshii* cells. Therefore, PhTET4 can advantageously work at high temperature required by industrial fermentation process.

d) Inhibition of PhTET4 Amidolytic Activity Using EDTA

In case of PhTET1, 2 and 3 aminopeptidases, it has been shown that the two metal ions present in the catalytic site are essential both for catalysis and for assembling the dodecameric edifice. For this reason, treatment with the divalent ions chelating agent EDTA leads to the dissociation of the TET quaternary structures and to enzymes inactivation. Indeed, in the optimal conditions for PhTET4 activity, the addition of 5 mM EDTA completely inhibited the glycine aminopeptidase activity. However, analysis of the oligomeric state of EDTA-treated PhTET4 samples by size-exclusion chromatography revealed that the PhTET4 dodecameric edifice remained unaffected by the EDTA treatment unlike what was reported for all the other TET enzymes (FIG. 6). This suggests that the contribution of the metals ions situated in position M1 and/or M2 for PhTET4 oligomerization is not as important as for the other TET peptidases.

e) Amidolytic Activity of PhTET4 Using Optimal Operation Conditions

The initial characterization of PhTET4 aminopeptidase activity indicated that the enzyme displayed narrow substrate specificity with a strong preference for glycine residues. In order to consolidate this finding, the experiments were repeated in the presence of nickel and in the optimal temperature and pH conditions defined above (0.1 mM NiCl2, pH 9.5 and at 85° C.), and results are represented in FIG. 7. These results show unambiguously that the enzyme acted only on Gly-pNA. No hydrolytic activity could be detected toward all other amino acids, even with long incubation times. This confirms the previous results.

The inventors also tried to investigate if PhTET4 exhibits high D-stereospecificity against D-Alanine as shown for *Aspergillus oryzae* glycine aminopeptidase (Marui, J., et al.

(2012)). For this, D-Ala-pNA was used as chromogenic substrate in optimal activity conditions (0.1 mM $NiCl_2$, pH 9.5 and 85° C.) and the results are reported in FIG. 7. The experiment showed that PhTET4 is unable to cleave residue alanine in D-conformation, thus demonstrating that PhTET4 is devoid from D-stereospecificity.

5. Endopeptidase and Exopeptidase Activities of PhTET4

In aminopeptidases, it is known that the catalytic activities and specificities can be affected by the length and N-terminal amino acid composition of the peptide substrate. Consequently, the inventors tested if PhTET4 maintains its narrow specificity toward glycine residues in a peptide context. For this, the inventors measured PhTET4 capacity to cleave N-terminal residue of the following peptides: GI; GL; GLM; GMDSLAFSGGL and LGG. After incubation of PhTET4 with the peptide substrates in optimal activity conditions (0.1 mM NiCl2, pH 9.5 and 85° C.), the reaction products were separated by reverse phase HPLC and identified by N-terminal sequencing.

The HPLC chromatographic profiles of the degradation of GLM and GMDSLAFSGGL peptides are shown on FIGS. 8A and 8B, respectively. The sequences of the detected accumulating peptides were determined and the results clearly demonstrated that PhTET4 does not exert amidolytic activity beyond the N-ter glycine in a peptide context. Therefore, PhTET4 is exclusively an exopeptidase. Overall, the results of these experiments showed that no enzymatic activity was detected against peptide that do not start by glycine residue even if a glycine residue is present at P1' position as demonstrated with the LGG tripeptide.

To assess if PhTET4 can process consequently several glycine residues in a peptide sequence, the inventors tested the enzymatic activity against the chromogenic peptide Gly-Gly-pNA in the same conditions as described previously. In the results, PhTET4 displayed significant activity against this substrate, corresponding to 10% of the total activity exhibited in presence of monoacyl compound Gly-pNA. Taken together, these experiments clearly mark PhTET4 as an aminopeptidase strictly specialized in the hydrolysis of N-terminal glycine residues.

BIBLIOGRAPHY

Jamdar, S. N. (2009) A novel aminopeptidase from *Burkholderia cepacia* specific for acidic amino acids. FEMS Microbiol Lett 295, 230-237

Marui, J., Matsushita-Morita, M., Tada, S., Hattori, R., Suzuki, S., Amano, H., Ishida, H., Yamagata, Y., Takeuchi, M., and Kusumoto, K. (2012) Enzymatic properties of the glycine D-alanine [corrected] aminopeptidase of *Aspergillus oryzae* and its activity profiles in liquid-cultured mycelia and solid-state rice culture (rice koji). Applied microbiology and biotechnology 93, 655-669

Ito K, Ma X, Azmi N, Huang H S, Fujii M, Yoshimoto T. (2003) Novel aminopeptidase specific for glycine from *Actinomucor elegans*. Biosci Biotechnol Biochem. January; 67(1):83-8

What is claimed is:

1. A method for the modification of all or part of the polypeptide content of a substrate comprising peptides, polypeptides and/or proteins harbouring a N-terminus glycine residue, comprising contacting all or part of the substrate, peptides, polypeptides and/or proteins harbouring a N-terminus glycine residue, with at least a TET protein harbouring at least a N-terminus glycine residues specific exopeptidase activity, said at least TET protein comprising the amino acid sequence as set forth in SEQ ID NO: 1, or with any homologous protein derived from said at least TET protein as set forth in SEQ ID NO: 1 by substitution, addition or deletion of at least one amino acid, provided that the derived protein retains at least 79% of identity with the amino acid sequence as set forth in SEQ ID NO: 1, and said derived protein retaining a N-terminus glycine residues specific exopeptidase activity.

2. The method according to claim 1, wherein said TET protein or said derived protein originates from an extremophilic microorganism belonging to the *Thermococcales* order.

3. The method according to claim 2, wherein said extremophilic microorganism is *Pyrococcus horikoshii*.

4. The method according to claim 1, wherein peptides, polypeptides and/or proteins of said substrate are obtained from food industry or health industry or chemical industry.

5. The method according to claim 1, wherein peptides, polypeptides and/or proteins of said substrate are proteins from fermented products or soya products or sea food products or cheese products.

6. The method according to claim 1, wherein peptides, polypeptides and/or proteins of said substrate are proteins obtained from dairy products, fruit juices, beers, flours or cured products, from wine industry products, from cheese products, or sea food products.

7. The method according to claim 1, which comprises contacting said polypeptide harbouring a N-terminus glycine residue with at least a TET protein harbouring at least a N-terminus glycine residues specific exopeptidase activity, said TET protein comprising the amino acid sequence as set forth in SEQ ID NO: 1, or at least one homologous protein derived from said TET protein as set forth in SEQ ID NO: 1 by substitution, addition or deletion of at least one amino acid, provided that the derived protein retains at least 79% of identity with the amino acid sequence as set forth in SEQ ID NO: 1, and said derived protein retaining a N-terminus glycine residues specific exopeptidase activity, and optionally recovering the resulting N-terminal glycine free peptides.

8. The method according to claim 1, which comprises contacting said substrate with at least a TET protein harbouring at least a N-terminus glycine residues specific exopeptidase activity, said TET protein comprising the amino acid sequence as set forth in SEQ ID NO: 1, or at least one homologous protein derived from said TET protein as set forth in SEQ ID NO: 1 by substitution, addition or deletion of at least one amino acid, provided that the derived protein retains at least 79% of identity with the amino acid sequence as set forth in SEQ ID NO: 1, and said derived protein retaining a N-terminus glycine residues specific exopeptidase activity, and optionally recovering the modified polypeptide content of said substrate.

9. The method according to claim 1, wherein said contacting comprises the activation of the said TET protein or derived protein using as enzyme cofactor at least one of the metal ions of the group comprising : $Ni^{2+}$, $Co^{2+}$, $Mn^{2+}$.

10. The method according to claim 1, wherein said contacting is carried out from pH 9 to pH 10.

11. The method according to claim 1, wherein said contacting is carried out from 80° C. to 100° C.

12. The method according to claim 1, wherein said at least TET protein or said derived protein is immobilized on a solid support.

13. The method according to claim 12, wherein said solid support is a filter cartridge or silica beads or magnetic beads or on organic polymeric materials, or on inorganic polymeric materials or on membrane devices or in microcapsules.

14. The method according to claim 12, wherein peptides, polypeptides and/or proteins of said substrate are obtained from food, chemical and health industries, or from biomass.

* * * * *

SEQUENCE LISTING

```
Sequence total quantity: 6
SEQ ID NO: 1            moltype = AA  length = 336
FEATURE                 Location/Qualifiers
source                  1..336
                        mol_type = protein
                        organism = Pyrococcus horikoshii
SEQUENCE: 1
MERIVKILRE ILEIPSPTGY TKEVMSYLEK FLKENEVNFY YTNKGALIAG NHPKPELVVI   60
AHVDTLGAMV KEILPDGHLA FSRIGGLVLP TFEGEYCTII TRKGKKFRGT LLLRNPSAHV  120
NREVGKKERK EENMYIRLDE LVEKREDTEK LGIRPGDFIA FDPKFEYVNG FVKSHFLDDK  180
ASVAAILDLI IDMKDELEKY PVAFFFSPYE EVGHGGSAGY PPTTKELLVV DMGVVGEGVS  240
GKETAVSIAA KDTTGPYDYD MTNRLIELAE ENNIPYVVDV FPYYGSDGSA ALRAGWDFRV  300
ALIGPGVHAS HGMERTHVKG LLATKELIRA YIKWKG                            336

SEQ ID NO: 2            moltype = AA  length = 332
FEATURE                 Location/Qualifiers
source                  1..332
                        mol_type = protein
                        organism = Pyrococcus horikoshii
SEQUENCE: 2
MMSMIEKLKK FTQIPGISGY EERIREEIIR EIKDFADYKV DAIGNLIVEL GEGEERILFM   60
AHMDEIGLLI TGITDEGKLR FRKVGGIDDR LLYGRHVNVV TEKGILDGVI GATPPHLSLE  120
RDKSVIPWYD LVIDIGAESK EEALELVKPL DFAVFKKHFS VLNGKYVSTR GLDDRFGVVA  180
LIEAIKDLVD HELEGKVIFA FTVQEEVGLK GAKFLANHYY PQYAFAIDSF ACCSPLTGDV  240
KLGKGPVIRA VDNSAIYSRD LARKVWSIAE KNGIEIQIGV TGGGTDASAF QDRSKTLALS  300
VPIKYLHSEV ETLHLNDLEK LVKLIEALAF EL                                332

SEQ ID NO: 3            moltype = AA  length = 353
FEATURE                 Location/Qualifiers
source                  1..353
                        mol_type = protein
                        organism = Pyrococcus horikoshii
SEQUENCE: 3
MEVRNMVDYE LLKKVVEAPG VSGYEFLGIR DVVIEEIKDY VDEVKVDKLG NVIAHKKGEG   60
PKVMIAAHMD QIGLMVTHIE KNGFLRVAPI GGVDPKTLIA QRFKVWIDKG KFIYGVGASV  120
PPHIQKPEDR KKAPDWDQIF IDIGAESKEE AEDMGVKIGT VITWDGRLER LGKHRFVSIA  180
FDDRIAVYTI LEVAKQLKDA KADVYFVATV QEEVGLRGAR TSAFGIEPDY GFAIDVTIAA  240
DIPGTPEHKQ VTHLGKGTAI KIMDRSVICH PTIVRWLEEL AKKHEIPYQL EILLGGGTDA  300
GAIHLTKAGV PTGALSVPAR YIHSNTEVVD ERDVDATVEL MTKALENIHE LKI         353
```

```
SEQ ID NO: 4           moltype = AA  length = 354
FEATURE                Location/Qualifiers
source                 1..354
                       mol_type = protein
                       organism = Pyrococcus horikoshii
SEQUENCE: 4
MDLKGGESMV DWKLMQEIIE APGVSGYEHL GIRDIVVDVL KEVADEVKVD KLGNVIAHFK    60
GSSPRIMVAA HMDKIGVMVN HIDKDGYLHI VPIGGVLPET LVAQRIRFFT EKGERYGVVG   120
VLPPHLRRGQ EDKGSKIDWD QIVVDVGASS KEEAEEMGFR VGTVGEFAPN FTRLNEHRFA   180
TPYLDDRICL YAMIEAARQL GDHEADIYIV GSVQEEVGLR GARVASYAIN PEVGIAMDVT   240
FAKQPHDKGK IVPELGKGPV MDVGPNINPK LRAFADEVAK KYEIPLQVEP SPRPTGTDAN   300
VMQINKEGVA TAVLSIPIRY MHSQVELADA RDVDNTIKLA KALLEELKPM DFTP         354

SEQ ID NO: 5           moltype = DNA  length = 1011
FEATURE                Location/Qualifiers
source                 1..1011
                       mol_type = genomic DNA
                       organism = Pyrococcus horikoshii
SEQUENCE: 5
atggaaagga tagtcaagat cttaagggaa atcttagaga taccttctcc aacgggctac    60
acgaaggagg taatgagtta cctagaaaaa tttctaaagg aaaatgaagt aaactttttac  120
tatacgaaca aggggggccct aatagccggt aatcatccaa agcctgagct cgttgttata  180
gcccacgtag acacgcttgg ggcaatggtt aaggagatac taccagacgg acacttagca   240
ttttcaagga taggagggct cgttctacct acgtttgaag gcgaatactg tactataata   300
acgagaaaag gaaagaagtt tagaggaacg ctcctcctta gaaatccgag cgctcatgta   360
aatagggaag taggtaaaaa ggagagaaaa gaggagaata tgtatataag attggacgag   420
ctcgtggaga agagagagga tacagaaaag ctggggataa ggccaggaga cttcatagct   480
tttgatccca aatttgaata cgtaaacggc tttgttaaat cacacttcct agatgacaag   540
gctagcgtag ctgcaatact cgatctaata atagatatga aggatgaact cgagaagtat   600
ccagttgcat tcttcttctc accgtatgag gaagttggcc acggaggctc agctggctac   660
ccaccaacga ctaaggaact gctcgtggtt gatatgggag tagtgggtga aggtgtttca   720
ggaaaagaaa ccgccgtatc tatagcggcc aaggatacaa ctgggcctta tgactatgac   780
atgacgaaca ggttaataga gcttgctgaa gagaacaata tcccatatgt agttgacgtg   840
ttcccctact atggttccga tggttcagct gcactaagag ctggatggga tttcaggggtt  900
gccctaattg ggccaggtgt gcacgcaagc cacggaatgg agagaaccca cgttaaggga   960
ttgttggcaa ctaaagagct tataagggct tacataaaat ggaaggggta a           1011

SEQ ID NO: 6           moltype = AA  length = 11
FEATURE                Location/Qualifiers
REGION                 1..11
                       note = Generated peptide for amidolytic activity assay
source                 1..11
                       mol_type = protein
                       organism = synthetic construct
SEQUENCE: 6
GMDSLAFSGG L                                                         11
```